United States Patent
Evans et al.

(10) Patent No.: US 10,894,031 B2
(45) Date of Patent: Jan. 19, 2021

(54) POLYPHENOL-REACTIVE OXYGEN SPECIES COMPOSITIONS AND METHODS

(71) Applicant: PowerGut, Inc., San Anselmo, CA (US)

(72) Inventors: Michael Evans, Palo Alto, CA (US); Robert Wotring, Palo Alto, CA (US)

(73) Assignee: PowerGut, INC., San Anselmo, CA (US)

( * ) Notice: Subject to any disclaimer, the term of this patent is extended or adjusted under 35 U.S.C. 154(b) by 0 days.

(21) Appl. No.: 16/143,398

(22) Filed: Sep. 26, 2018

(65) Prior Publication Data

US 2019/0022056 A1    Jan. 24, 2019

Related U.S. Application Data

(63) Continuation of application No. 14/404,612, filed as application No. PCT/US2013/043249 on May 30, 2013, now abandoned.

(60) Provisional application No. 61/782,833, filed on Mar. 14, 2013, provisional application No. 61/653,118, filed on May 30, 2012.

(51) Int. Cl.

| | | |
|---|---|---|
| *A61K 31/353* | (2006.01) | |
| *A61K 36/82* | (2006.01) | |
| *A61K 31/7048* | (2006.01) | |
| *A61K 31/366* | (2006.01) | |
| *A61K 36/185* | (2006.01) | |
| *A61K 33/40* | (2006.01) | |
| *A23L 33/105* | (2016.01) | |

(52) U.S. Cl.
CPC .......... *A61K 31/353* (2013.01); *A23L 33/105* (2016.08); *A61K 31/366* (2013.01); *A61K 31/7048* (2013.01); *A61K 33/40* (2013.01); *A61K 36/185* (2013.01); *A61K 36/82* (2013.01); *A23V 2002/00* (2013.01)

(58) Field of Classification Search
None
See application file for complete search history.

(56) References Cited

U.S. PATENT DOCUMENTS

2010/0158885 A1* 6/2010 Huang .................... A61K 38/44
424/94.2

FOREIGN PATENT DOCUMENTS

WO    WO-2006079109 A2 *    7/2006   ........... A61K 31/353

OTHER PUBLICATIONS

Google Patent Search_Feb. 19, 2020_composition comprising pomegranate polyphenol (-wonderful) (Year: 2020).*
Google Scholar Search_Feb. 20, 2020_pomegranate rind extract puniclagin (Year: 2020).*
N. Seeram, R. Lee, M. Hardy, D. Heber. Rapid large scale purification of ellagitannins from pomegranate husk, a by-product of the commercial juice industry. Separation and Purification Technology 41 (2005) 49-55) (Year: 2005).*

* cited by examiner

*Primary Examiner* — Michael P Cohen
(74) *Attorney, Agent, or Firm* — Shirley A. Recipon

(57) ABSTRACT

Disclosed herein are nutraceutical compositions comprising or consisting essentially of one or more types of polyphenols (e.g., a green tea polyphenol) and one or more types of reactive oxygen species, and methods for their use to treat gastrointestinal conditions, inflammatory conditions, and immune conditions.

15 Claims, 1 Drawing Sheet

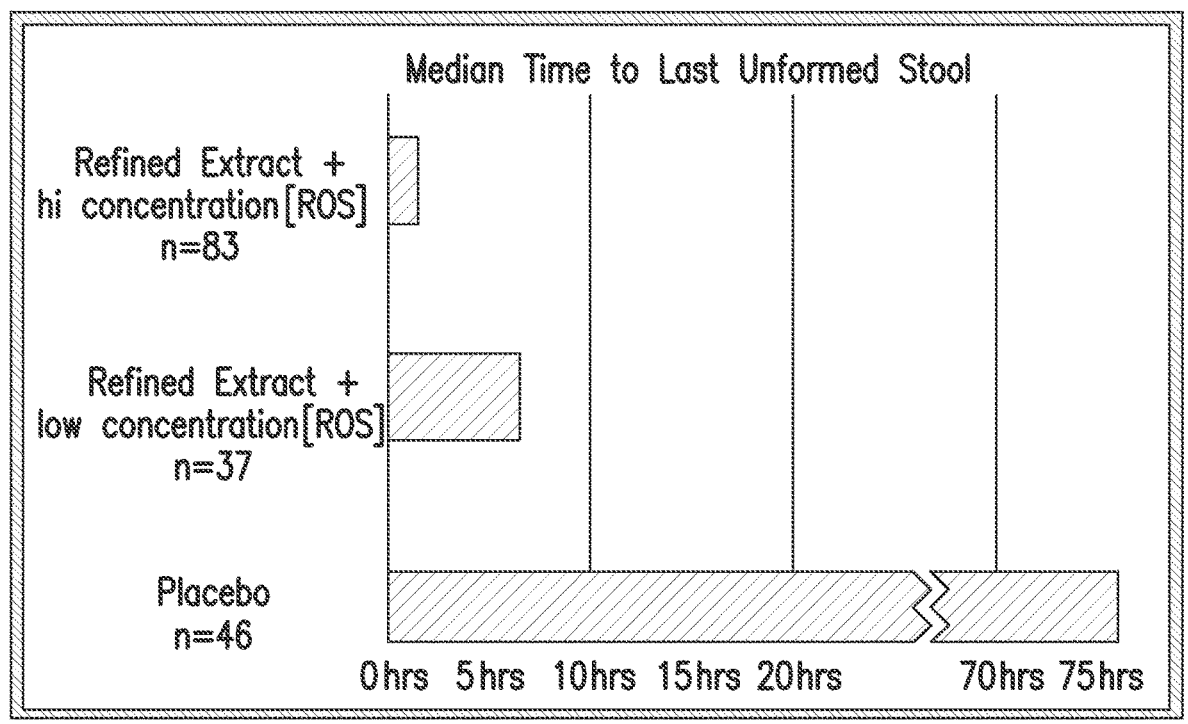

POLYPHENOL-REACTIVE OXYGEN SPECIES COMPOSITIONS AND METHODS

RELATED APPLICATION APPLICATIONS

This application is a continuation of U.S. application Ser. No. 14/404,612, filed Nov. 29, 2014, which is a U.S. national phase application of PCT Application No. PCT/US2013/043249, filed May 30, 2013, which claims priority to U.S. Provisional Application Ser. No. 61/653,118, filed May 30, 2012, and U.S. Provisional Application Ser. No. 61/782,833, filed Mar. 14, 2013, all of which are hereby incorporated-by-reference.

INCORPORATION BY REFERENCE

The patents, patent applications, and publications cited herein are hereby incorporated by reference in their entirety. The disclosures of these publications in their entireties are hereby incorporated by reference into this application in order to more fully describe the state of the art as known to those skilled therein as of the date of the invention described and claimed herein.

This patent disclosure contains material that is subject to copyright protection. The copyright owner has no objection to the facsimile reproduction by anyone of the patent document or the patent disclosure as it appears in the U.S. Patent and Trademark Office patent file or records, but otherwise reserves any and all copyright rights.

BACKGROUND OF THE INVENTION

A number of pharmaceutical agents have been developed for treatment of gastrointestinal, inflammatory, and immune conditions. These pharmaceutical agents have both beneficial and adverse effects, such as drowsiness, mood, nausea, vomiting, cardiovascular, renal, gastrointestinal, skeletal, and others. The adverse effects and lack of efficacy of current pharmaceutical agents indicate a continuing need for new and more effective anti-microbial, anti-inflammatory and immune-modulating compositions that can be safely administered long with few, if any, adverse reactions.

SUMMARY OF THE INVENTION

Disclosed herein are nutraceutical compositions, kits, and methods for treating gastrointestinal, inflammatory, and immune conditions.

Accordingly, in one aspect described herein is nutraceutical composition comprising or consisting essentially of at least one polyphenol in combination with at least one reactive oxygen species ("ROS"), wherein the composition comprises an effective amount of the at least one polyphenol and the at least one reactive oxygen species to treat an animal or human subject suffering from a gastrointestinal condition, an inflammatory condition, an immune condition, and internal or topical infection, urinary tract conditions, or respiratory conditions. As used herein, the nutraceutical composition that "consists essentially of" an effective amount of at least one polyphenol and at least one reactive oxygen species refers to the nutraceutical's active ingredients towards the relevant condition, i.e., gastrointestinal, inflammatory, or immune conditions, such that the composition's active ingredients consists of at least one polyphenol and at least one reactive oxygen species, and such that the nutraceutical can also contain inactive ingredients, for example, preservatives, stabilizers, flavorings, colorings, non-polyphenol substances from a plant extract that can be solubilized into solution, nutritional additives (such as vitamins, minerals, and the like) and substances for pH adjustment.

In some embodiments, the nutraceutical composition is provided as an aqueous solution. In other embodiments, the nutraceutical composition is provided as a gel, powder, aerosol, mist, spray film, ointment, time-release compound, or suppository.

In some embodiments, the nutraceutical composition comprises or consists essentially of an effective amount of the at least one polyphenol and the at least one reactive oxygen species to treat a subject suffering from: an acute or chronic gastrointestinal condition (e.g., gastrointestinal condition is diarrhea, Crohn's disease, diverticulosis, diverticulitis, *Helicobacter pylori* (stomach infection), lactose intolerance, Irritable Bowel Syndrome (IBS), ulcerative colitis, colon polyps and cancer, or unexplained abdominal pain); an inflammatory condition (e.g., asthma, sinusitis, otitis media, or bacterial conjunctivitis or infections, an autoimmune disease, rheumatoid arthritis, sarcoidosis, celiac disease, vasculitis, or interstitial cystis); an immune condition (e.g., lupus, multiple sclerosis, Type 1 diabetes, allergies, Graves' disease, scleroderma, eosinophilic gastroenteritis, Hashimoto's thyroiditis, or inclusion body myositis).

In other embodiments, the nutraceutical composition comprises or consists essentially of an effective amount of the at least one polyphenol and at least one reactive species to treat a subject suffering from the effects of chronically elevated systemic levels of serotonin, such as osteoporosis.

In other embodiments, the nutraceutical composition comprises or consists essentially of an effective amount of at least one polyphenol and at least one reactive oxygen species to treat a subject suffering from the side effects of elevated systemic serotonin levels secondary to various medicines, such as selective serotonin reuptake inhibitors (SSRIs), which lead to gastrointestinal symptoms such as nausea, vomiting, diarrhea, gas & bloating, GERD (gastroesophageal reflux disease), upset stomach.

In some embodiments, the nutraceutical composition comprises or consists essentially of an effective amount of at least one polyphenol and at least one reactive oxygen species to provide inhibition or modulation of epithelial ion transport in order to treat a subject suffering from intestinal effects such as diarrhea, nausea, vomiting, gas and bloating, GERD, upset stomach, lactose intolerance, Irritable Bowel Syndrome (IBS), ulcerative colitis, or the like, due to intestinal crypt fluid secretion.

Most plants live in close relationship with microbial partners or symbionts, which provide nutrients and thereby assist their host to grow. The involvement of polyphenols, including flavonoids, in several host-pathogen interactions has been suggested. These compounds are often stored at strategically important sites, where they may play a signalling and/or a direct role in defense. For example, the role of barley flavonoids in resistance against *Fusarium* may be related to 1) the crosslinking of microbial enzymes; the inhibition of microbial cellulases, xylanases, pectinases; 3) chelation of metals necessary for enzyme activity, and 4) the formation of a physical barrier against pathogen attack.

In addition to these direct defense mechanisms, several polyphenols, including flavonoids, exuded from plants act as signals that attract and promote colonization by certain bacterial species while deterring and inhibiting the growth of others. Flavonoids may also act as attractant molecules for microorganisms and as inducers of genes that promote their survival by inducing transcription of bacterial genes, where protein products are necessary for critical processes for plant growth.

$H_2O_2$ takes part in resistance mechanisms by reinforcing of the plant cell wall via lignification and cross-linking of cell wall structural proteins. $H_2O_2$ is also involved in phytoalexin production and resistance enhancement. In plant-microbe interaction, $H_2O_2$ production in plants can kill the pathogen directly or induce plant defense genes or other resistance genes to limit infection by the microbe.

Human gastrointestinal mucosal surfaces, as well as those of other animals are inhabited by microbial populations, which are commonly referred to as the 'commensal flora'. The long-term maintenance of microbial complexity on mucosal surfaces is extraordinary, as the flora consists of microbes with vastly different growth characteristics and nutritional and metabolic needs. There are several innate inhibitory mechanisms in place to limit both commensal and pathogenic microbial growth. For example, Paneth cells, which are a specialized epithelial cell population that reside in intestinal crypts, express bactericidal proteins that include lysozyme, cryptdins and angiogenin. In addition to these innate mechanisms, it is becoming increasingly evident that the diet of humans and other animals has a profound impact on viability of both the commensal and pathogenic species.

Commensal flora provide an important layer of defense against invasion by pathogenic microbes, and small changes to their complexity and/or density may create an environment that renders the host more susceptible to pathogenic species. Altering the intestinal commensal flora by the contents of foods that act inhibit or enhance the survivability of intestinal microbes may reduce or increase the likelihood of pathogenic species, and in doing so increase the likelihood of, or prevent certain diseases.

The interactions between microbes and the mammalian host are complex and this is particularly true for a subset of microbe, such as *Bacteroides*, which enhance the development of the adaptive immune system when confined to the lumen of the intestinal tract, but becomes pathogenic when it traverses the mucosal epithelium.

Quorum Sensing (QS) is a regulatory mechanism that enables bacteria to make collective decisions with respect to the expression of a specific set of genes. Many pathogenic bacteria trigger the production of their virulence factors in a population density-dependent manner involving cell-to-cell communication QS. This mechanism enables bacteria to detect their population density through the production, release, and perception of small diffusible molecules called autoinducers and to coordinate gene expression accordingly. QS mechanisms amplify bacterial virulence by stimulating the expression of disease causing attributes, such as motility, biofilm formation, and secretion of virulence factors. The inhibition of QS systems is considered to be a potential way to reduce the virulence of pathogenic bacteria.

It has been reported that flavonoids might inhibit QS mechanisms, cell-cell signaling, and biofilm formation in *Vibrio harveyi* and *E. coli* O157:H7. It has also been suggested that catechin inhibits QS by down-regulating the expression levels of N-acylhomoserine lactone (AHL) synthase its associated regulator genes. Epigallocatechin gallate has been reported to repress the expression of virulence factors for *P. aeruginosa* in *P. putida* cells hosting the pKR-C12 plasmid and the expression of luxI from Photobacterium *fischeri* in *E. coli* cells hosting the pSB403 plasmid.

In addition to QS inhibition by flavonoids, other phenolic compounds such as urolithin-B, an ellagitanin-derived metabolite, also inhibited the production of AHLs which led to reduced swimming mobility and the ability to form biofilms in the enteropathogen *Y. enterocolitica*. Urolithin-A has been demonstrated to induce the growth of *Bifidobacterium. Lactobacillus*, and Clostiridium while decreasing the counts of total enterobacteria and, in particular, of *E. coli*. It has been proposed that the decrease in the pathogens growth may be a consequence of the parallel induction of some of the beneficial bacteria.

Testing whether a composition, with at least one polyphenol and at least one reactive oxygen species, can provide inhibition of epithelial ion transport can be conducted with in vitro cell models for chloride ion secretion or short-circuit current with respect to ion secretion as known in the art (i.e., such as the use of T84 human intestinal cells, see Tradtrantip, L., et al., *Molecular Pharmacology*, 2010, 77:69-78).

In some embodiments, the nutraceutical composition comprises or consists essentially of an effective amount of at least one polyphenol and at least one reactive oxygen species to treat a subject suffering from diarrhea. In one embodiment, the nutraceutical composition consists essentially of an effective amount of the at least one polyphenol and the reactive oxygen species to treat a subject suffering from diarrhea such that the subject does not have an unformed stool (i.e., the time to the last unformed stool after ingestion of the composition) later than about 5 minutes to about 6.5 hours after ingestion of the nutraceutical composition, e.g., about 5 minutes, 15 minutes, 30 minutes, 45 minutes, 1 hour, 2 hours, 2.5 hours, 3 hours, 4 hours, 4.5 hours, 5 hours, 5.5 hours, 6 hours, 6.5 hours, or another period from about 5 minutes to about 6.5 hours following ingestion of the nutraceutical composition.

In other embodiments, the nutraceutical composition comprises or consists essentially of from about 0.001% to about 0.009%, from about 0.002% to about 0.008%, from about 0.003% to about 0.007%, from about 0.004% to about 0.006%, from about 0.003% to about 0.005%, or about 0.004% of at least one polyphenol, and from about 0.01% to less than 1%, from about 0.01% to about 0.5%, from about 0.01% to about 0.09%, from about 0.02% to about 0.08%, from about 0.03% to about 0.08%, from about 0.03% to about 0.07%, from about 0.04% to about 0.08%, from about 0.04% to about 0.07%, about 0.05%, about 0.06%, or about 0.07% of at least one reactive oxygen species, wherein after oral administration of the nutraceutical composition to a subject suffering from diarrhea, the subject does not have an unformed stool (i.e., the time to the last unformed stool after ingestion of the composition) as soon as about 5 minutes to about 6.5 hours after ingestion of the nutraceutical composition. As used herein, when the term "about" refers to a numeric value relating to a polyphenol or a reactive oxygen species, the term "about" means a range of plus or minus four-tenths of the value. For example, a value of about 0.001% to about 0.009% means 0.0006-0.0014% to 0.0086-0094%.

In other embodiments, the nutraceutical composition comprises or consists essentially of from about 0.001% to about 0.009%, from about 0.002% to about 0.008%, from about 0.003% to about 0.007%, from about 0.004% to about 0.006%, from about 0.003% to about 0.005%, or about 0.004% of at least one polyphenol, and from about 0.01% to less than 1%, from about 0.01% to about 0.5%, from about 0.01% to about 0.09%, from about 0.02% to about 0.08%, from about 0.03% to about 0.08%, from about 0.03% to about 0.07%, from about 0.04% to about 0.08%, from about 0.04% to about 0.07%, about 0.05%, about 0.06%, or about 0.07% of hydrogen peroxide, wherein after oral administration of the nutraceutical composition to a subject suffering from diarrhea, the subject does not have an unformed stool as soon as about 5 minutes to about 6.5 hours after ingestion of the nutraceutical composition.

In some embodiments, the at least one reactive oxygen species in the nutraceutical composition is present in an amount sufficient to synergize with the at least one polyphenol such that a subject suffering from diarrhea who ingests the nutraceutical composition is prevented from having an unformed stool at least 2-fold, 3-fold, 4-fold, 5-fold, 6-fold, 7-fold, 8-fold, 9-fold, or 10-fold or more faster as compared to a subject suffering from diarrhea who ingests a nutraceutical composition that does not comprise a reactive oxygen species and/or does not comprise at least one polyphenol. In these embodiments, the nutraceutical composition can comprise or consist essentially of from about 0.001% to about 0.009%, from about 0.002% to about 0.008%, from about 0.003% to about 0.007%, from about 0.004% to about 0.006%, from about 0.003% to about 0.005%, or about 0.004% of at least one polyphenol, and from about 0.01% to less than 1%, from about 0.01% to about 0.5%, from about 0.01% to about 0.09%, from about 0.02% to about 0.08%, from about 0.03% to about 0.08%, from about 0.03% to about 0.07%, from about 0.04% to about 0.08%, from about 0.04% to about 0.07%, about 0.05%, about 0.06%, or about 0.07% of at least one reactive oxygen species. In certain of these embodiments, the at least one reactive oxygen species that provides a synergistic effect is hydrogen peroxide.

In some embodiments, the invention provides a liquid nutraceutical composition comprising or consisting essentially of at least one polyphenol present at a concentration of about 0.004% and at least one reactive oxygen species present at a concentration of about 0.05% or about 0.06%, wherein when orally administered to a subject suffering from acute gastroenteritis the subject does not have an unformed stool as soon as about 1.5 hours. In one embodiment, the polyphenols are from refined extracts derived from crude green tea and pomegranate rind extracts. In one embodiment, the at least one reactive oxygen species is hydrogen peroxide.

In some embodiments, the invention provides a liquid nutraceutical composition comprising or consisting essentially of at least one polyphenol present at a concentration of about 0.004% and at least one reactive oxygen species present at a concentration of about 0.01% or about 0.02%, wherein when orally administered to a subject suffering from acute gastroenteritis the subject does not have an unformed stool as soon as about 6.5 hours. In one embodiment, the polyphenols are from refined extracts derived from crude green tea and pomegranate rind extracts. In one embodiment, the at least one reactive oxygen species is hydrogen peroxide.

Generally, the effective amount of the at least one polyphenol is from about 0.001% (w/v) to about 20% (w/v), e.g., about 0.001%, 0.002%, 0.003%, 0.004%, 0.005%, 0.006%, 0.007%, 0.008%, 0.009%, 0.01%, 0.02%, 0.03%, 0.04%, 0.05%, 0.06%, 0.07%, 0.08%, 0.09%, 0.1%, 0.2%, 0.5%, 1%, 2%, 5%, 8, 8%, 11%, 14%, 16%, 17%, to about 20%, or another percent from about 0.001% (w/v) to about 20% (w/v). In other embodiments, the effective amount of the at least one polyphenol is from about 0.001% (w/w) to about 20% (w/w), e.g., about 0.001%, 0.002%, 0.003%, 0.004%, 0.005%, 0.006%, 0.007%, 0.008%, 0.009%, 0.01%, 0.02%, 0.03%, 0.04%, 0.05%, 0.06%, 0.07%, 0.08%, 0.09%, 0.1%, 0.2%, 0.5%, 1%, 2%, 5%, 8%, 11%, 14%, 16%, 17%, to about 20%, or another percent from about 0.001% (w/w) to about 20% (w/w). In other embodiments, the effective amount of the at least one polyphenol is from about 0.001% to about 1%, from about 0.002% to about 0.5%, from about 0.003% to about 0.3%, from about 0.003% to about 0.2%, or from about 0.003% to about 0.1%. In other embodiments, the at least one polyphenol is present in the nutraceutical composition at about: 0.001%, 0.002%, 0.003%, 0.004%, 0.005%, 0.006%, 0.007%, 0.008%, 0.009%, 0.01%, 0.02%, 0.03%, 0.04%, 0.05%, 0.06%, 0.07%, 0.08%, 0.09%6, 0.1%, 0.2%, 0.5%, 1%, 2%, 5%, 8%, 11%, 14%, 16%, 17%, 18%, 19%, or 20% (w/v) or (w/w).

In some embodiments, at least one reactive oxygen species in the above-mentioned nutraceutical compositions can be, for example, one or more of: hydrogen peroxide, nitric oxide, peroxyl radical, or peroxynitrite anion, singlet oxygen, or hydroxyl radical. Alternatively, the reactive oxygen species may be selected from oxidants, oxidizing agents, decoloring and bleaching agents used in foods or animal feeds. Alternatively, the reactive oxygen species may be a percarbonate, a perborate, sodium peroxide, calcium peroxide, a peroxymonosulfate, or a urea-peroxide complex. Alternatively, the reactive oxygen species may be hypochlorite, bromate, or iodate supplied as any of their respective sodium, potassium, or calcium salts. Alternatively, the reactive oxygen species may be a concentrated aqueous solution of hydrogen peroxide containing >10 weight percent of hydrogen peroxide. Alternatively, the reactive oxygen species may be ozone, oxone, or a dioxirane. Alternatively, the reactive oxygen species may be benzoyl peroxide, peroxy acetic acid, nitrogen dioxide, chlorine, chlorine dioxide or azodicarbonamide. The reactivity or activity of any of the forgoing may be modulated by pH adjustment or exposure to light.

In some embodiments, at least one reactive oxygen species in the nutraceutical composition ranges from about 0.001% to about 10% (w/v) or (v/v), e.g., about 0.001%, 0.005%, 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 1%, 2%, 4%, 5%, 6%, 7%, 8%, to about 10%, or another percentage range (w/v) or (v/v) of the reactive oxygen species within 0.001-10%. In some embodiments, the at least one reactive oxygen species is present in the nutraceutical composition at about: 0.001%, 0.005%, 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 1%, 2%, 4%, 5%, 6%, 7%, 8%, 9%, or 10% (w/v) or (w/w).

In one embodiment, the reactive oxygen species to be combined with the at least one polyphenol is hydrogen peroxide at a final concentration (v/v) or (w/v) or (w/w) in the composition of from about 0.01% to about 0.9% or from about 0.001% to about 0.08%. In one embodiment, the reactive oxygen species to be combined with the at least one polyphenol is hydrogen peroxide at a final concentration in the composition of about 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, of hydrogen peroxide.

In some embodiments, the at least one polyphenol is a polyphenol found in green tea, black tea, pomegranate, acai, blackberries, blueberries, raspberries, rosemary, berberine, *Berberis* sp., *Garcinia* spp., Chinese gall nut, *Gallae chinensis, Rhus chinensis, Rhus semialata* galls, ginger, grape seed, sage, or any combination thereof. In other embodiments, the at least one polyphenol is a green tea (*Camelia sinensis*) polyphenol (e.g., epicatechin, epicatechin gallate, epigallocatechin, or epigallocatechin gallate), or any combination of these or synthetic analogs thereof. In some embodiments, the at least one polyphenol is a benzoquinone, a phenolic acid, an acetophenone, a phenylacetic acid, a hydroxycinnaminic acid, a coumarin, a phenylpropane, a chromone, a naphtoquinone, a xanthone, a stilbene, an anthroquinone, a flavonoid, an isoflavonoid, a lignan, a neolignan, a biflavonoid, a catechol melanin, or a condensed tanninpunicalagin, pedunculagin, punicaligin, flavanone, a flavone, flavonol, quercetin, an isoflavone, daidzein, genistein, hesperetin, naringenin, glycitein, eriodictyol, ellagic acid, chlorogenic acid, courmarin, or any combination of these or synthetic analogs thereof. In one embodiment the nutraceutical composition is a gel or powder. In some embodiments, the nutraceutical composition comprises: (1) a plant extract(s) that comprises one or more polyphenols, (2) at least one reactive oxygen species, and (3) water. The plant extract(s) generally comprise more than 50% polyphenols. In some embodiments, the nutraceutical composition is a clear, homogeneous solution that comprises one or more plant extracts each comprising one or more polyphenols, one or more reactive oxygen species, and water. In some embodiments, the nutraceutical composition can further comprise colorings, flavorings, additives, preservatives, vitamins, minerals, etc. In one embodiment, the nutraceutical composition further comprises potassium sorbate, sodium dihydrogenphosphate, peppermint extract, phosphoric acid for pH adjustment of the composition to 4.5-5.0, or caffeine, or any combination thereof.

In another aspect provided herein is a nutraceutical composition obtained by a process that comprises combining in aqueous solution at least one polyphenol and a reactive oxygen species, to obtain the nutraceutical composition, wherein the nutraceutical composition comprises an effective amount of the at least one polyphenol to treat a subject suffering from a gastrointestinal condition, an inflammatory condition, or an immune condition, and wherein the reactive oxygen species is combined in an amount sufficient to oxidize at least 10% of the at least one polyphenol, wherein the process does not comprise the addition of an active oxidoreductase, catalase, peroxidase, phenoloxidase, tyrosinase, or metal catalyst in combination with the at least one polyphenol or the reactive oxygen species.

In some embodiments of the nutraceutical composition obtained by the above-mentioned process, the reactive oxygen species is combined in an amount sufficient to oxidize at least 5% to about 95% of the at least one polyphenol, e.g., at least about 6%, 7%, 10%, 12%, 15%, 25%, 30%, 40%, 60%, 70%, 75%, 85%, 90%, or another percent of the at least one polyphenol from at least about 5% to about 95%.

In some embodiments, the above-mentioned process to generate the nutraceutical composition further comprises a dilution step following oxidation of the polyphenol. In some embodiments the dilution step includes about a 1:30 fold to about a 1:1000 fold dilution, e.g., about a 1:30, 1:50, 1:100, 1:200, 1:300, 1:350, 1:500, 1:600, 1:700, 1:900, or another fold dilution from about 1:60 to 1:1000 fold. In other embodiments, the above-mentioned process to generate the nutraceutical composition comprises combining the at least one polyphenol and the reactive oxygen species for at least about one minute to about one hour prior to treatment of the subject, e.g., at least about 2 minutes, 3 minutes, 4 minutes, 5 minutes, 7 minutes, 10 minutes, 15 minutes, 20 minutes, 30 minutes, 35 minutes, 40 minutes, 50 minutes, or a another period from at least about 1 minute to about one hour prior to treatment of the subject in need thereof.

In another aspect provided herein are kits. In some embodiments the kit consists essentially of (i) a first container containing a volume of a first nutraceutically acceptable solution comprising at least one polyphenol; (ii) a second container comprising a volume of a second solution containing a reactive oxygen species; and (iii) instructions to mix the first solution and second solution to obtain a third solution, and to ingest the third solution to thereby treat the gastrointestinal condition, inflammatory condition, or immune condition; wherein the first or second container can accommodate the combined volume of the first solution and the second solution.

In yet another aspect provided herein is a method for treating a subject suffering from a gastrointestinal condition, an inflammatory condition, or an immune condition, the method comprising providing to the subject (i) a first container containing a volume of a first nutraceutically acceptable solution comprising at least one polyphenol; (ii) a second container comprising a volume of a second solution containing a reactive oxygen species; and (iii) instructions to mix the first solution and second solution to obtain a third solution, and to ingest the third solution to thereby treat the gastrointestinal condition, inflammatory condition, or immune condition, wherein the first or second container can accommodate the combined volume of the first solution and the second solution. In some embodiments the gastrointestinal condition is acute or chronic diarrhea, Crohn's disease, diverticulosis, diverticulitis, *Helicobacter pylori* (stomach infection), lactose intolerance, Irritable Bowel Syndrome (IBS), ulcerative colitis, colon polyps and cancer, and unexplained abdominal pain. In one embodiment, the gastrointestinal condition is acute or chronic diarrhea. In other embodiments, the inflammatory condition is asthma, sinusitis, otitis media, or bacterial conjunctivitis, an autoimmune disease, rheumatoid arthritis, sarcoidosis, celiac disease, vasculitis, or interstitial cystis. In other embodiments, the immune condition is lupus, multiple sclerosis, Type I diabetes, allergies, Graves' disease, scleroderma, eosinophilic gastroenteritis, Hashimoto's thyroiditis, or inclusion body myositis. In other embodiments, the nutraceutical composition comprises an effective amount of the at least one polyphenol and the reactive species to treat a subject suffering from the effects of chronically elevated systemic levels of serotonin, such as osteoporosis. In other embodiments, the nutraceutical composition comprises an effective amount of at least one polyphenol and the reactive species to treat a subject suffering from the side effects of elevated systemic serotonin levels secondary to various medicines, such as selective serotonin reuptake inhibitors (SSRIs), which lead to gastrointestinal symptoms such as nausea, vomiting, diarrhea, gas & bloating, GERD, upset stomach, and heartburn.

In some embodiments, the instructions provided to the subject state that the ingestion step is to be done within about one minute to about one hour following the mixing step. e.g., within about 3 minutes, 4 minutes, 5 minutes, 10 minutes, 12 minutes, 20 minutes, 30 minutes, 40 minutes, 50 minutes, or another period from about one minute to about one hour following the mixing step.

BRIEF DESCRIPTION OF THE DRAWINGS

FIG. 1 shows the results from a single dose, double-blind, placebo-controlled, 3-arm study for comparing the Time to Last Unformed Stool (TTLUS) in human children and adults diagnosed with acute gastroenteritis. (See Example 1 herein.) The top line of the graph, "Refined Extract+hi concentration [ROS] n=83", shows averaged results from 83 subjects treated with Arm 1 Test Material. The middle line of the graph, "Refined Extract+low concentration [ROS]

n="37", shows averaged results from 37 subjects treated with Arm 2 Test Material. The bottom line of the graph, "Placebo n=46", shows averaged results from 46 subjects treated with Arm 3 or Placebo Test Material.

DETAILED DESCRIPTION OF THE INVENTION

Disclosed herein are nutraceutical compositions comprising or consisting essentially of at least one polyphenol and at least one reactive oxygen species, kits, and methods for treating gastrointestinal, inflammatory, and immune conditions in humans and animals.

There is a continued interest in the potential therapeutic uses of polyphenols, and many studies, in vitro and in vivo, have demonstrated that polyphenols have measurable effects on animals including humans, at organ, cell, and molecular levels, supporting the potential use of polyphenols for certain conditions.

Unless defined otherwise, all technical and scientific terms used herein have the same meaning as is commonly understood to which the claimed subject matter belongs. In the event that there are a plurality of definitions for terms herein, those in this section prevail. All patents, patent applications, publications and published nucleotide and amino acid sequences (e.g., sequences available in GenBank or other databases) referred to herein are incorporated by reference. Where reference is made to a URL or other such identifier or address, it is understood that such identifiers can change and particular information on the internet can come and go, but equivalent information can be found by searching the internet Reference thereto evidences the availability and public dissemination of such information.

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

The section headings used herein are for organizational purposes only and are not to be construed as limiting the subject matter described.

Definition of standard chemistry terms may be found in reference works, including but not limited to, Carey and Sundberg "ADVANCED ORGANIC CHEMISTRY 4th ED." Vols. A (2000) and B (2001), Plenum Press, New York. Unless otherwise indicated, conventional methods of mass spectroscopy, NMR, HPLC, protein chemistry, biochemistry, recombinant DNA techniques and pharmacology.

Unless specific definitions are provided, the nomenclature employed in connection with, and the laboratory procedures and techniques of, analytical chemistry, synthetic organic chemistry, and medicinal and pharmaceutical chemistry described herein are those recognized in the field. Standard techniques can be used for chemical syntheses, chemical analyses, pharmaceutical preparation, formulation, and delivery, and treatment of patients. Reactions and purification techniques can be performed e.g., using kits of manufacturer's specifications or as commonly accomplished in the art or as described herein. The foregoing techniques and procedures can be generally performed of conventional methods and as described in various general and more specific references that are cited and discussed throughout the present specification.

It is to be understood that the methods and compositions described herein are not limited to the particular methodology, protocols, cell lines, constructs, and reagents described herein and as such may vary. It is also to be understood that the terminology used herein is for the purpose of describing particular embodiments only, and is not intended to limit the scope of the methods, compounds, compositions described herein.

The terms "effective amount" or "therapeutically effective amount," as used herein, refer to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system.

The term "nutraceutically acceptable," as used herein, refers a material, such as a diluent, which does not abrogate the biological activity or properties of the nutraceutical compositions described herein, is relatively nontoxic and, i.e., the material may be administered to an individual without causing undesirable biological effects or interacting in a deleterious manner with any of the components of the composition in which it is contained.

The term "polyphenol," as used herein, refers to any compound, whether naturally occurring or synthetic, characterized by the presence of multiple phenol structural units.

The terms "reactive oxygen species" or "ROS," as used herein, refer to reactive oxygen-containing molecules including those that can yield free radicals. Similarly, the terms "reactive oxygen species" or "ROS," as used herein, also encompass compounds which are classified as oxidants, oxidizing agents, decoloring agents and bleaching agents.

The terms "treat," "treating" or "treatment," as used herein, include alleviating, abating or ameliorating a disease or condition symptoms, preventing additional symptoms, ameliorating or preventing the underlying causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically. Further, the term applies whether the "treatment" is administered by a physician or other medical professional, or self-administered by the subject.

The singular forms "a", "an" and "the" include plural reference unless the context clearly dictates otherwise.

As used herein the term "about" is used herein to mean approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 percent up or down (higher or lower). When the term "about" refers to a numeric value relating to the amount of polyphenol or of a reactive oxygen species, the term "about" means a range of plus or minus four-tenths of the value. For example, a value of about 0.001% to about 0.009% means 0.0006-0.0014% to 0.0086-0094%.

As used herein, the term "Time to Last Unformed Stool (TTLUS)" refers to the amount of time after orally ingesting a nutraceutical composition of the invention a subject suffering from diarrhea (i.e., such as in acute gastroenteritis) has his or her last unformed stool. Herein, the TTLUS is also referred to as the amount of time after ingestion that the subject does not have an unformed stool, i.e., after the last unformed stool, the subject does not have an unformed stool.

Nutraceutical Compositions

Described herein are nutraceutical compositions comprising or consisting essentially of at least one polyphenol in combination with at least one reactive oxygen species, in which the composition contains an effective amount of the at least one polyphenol and the at least one reactive oxygen species to treat a subject suffering from a gastrointestinal condition, an inflammatory condition, or an immune condition. In some embodiments, the nutraceutical composition is provided as a solution. In other embodiments, the nutraceutical composition is provided as a powder or gel, which may also contain nutraceutically acceptable excipients known in the art.

In some cases, the at least one polyphenol includes multiple polyphenols, e.g., about 2 to about 100 polyphenols, e.g., 3, 5, 10, 20, 15, 30, 50, 60, 70, or another number of polyphenols from about 2 to about 100. Examples of polyphenols suitable for the nutraceutical compositions disclosed herein include, but are not limited to, epicatechin, epicatechin gallate, epigallocatechin, epigallocatechin gallatea benzoquinone, a phenolic acid, an acetophenone, a phenylacetic acid, a hydroxycinnaminic acid, a coumarin, a phenylpropane, a chromone, a naphtoquinone, a xanthone, a stilbene, an anthroquinone, a flavonoid, an isoflavonoid, a lignan, a neolignan, a biflavonoid, a catechol melanin, or a condensed tanninpunicalagin, pedunculagin, punicalin, flavanone, a flavone, flavonol, quercetin, an isoflavone, daidzein, genistein, hesperetin, naringenin, glycitein, eriodictyol, ellagic acid, courmarin, or any combination of these. In one embodiment, the nutraceutical composition includes at least one green tea polyphenol, e.g., epicatechin, epicatechin gallate, epigallocatechin, epigallocatechin gallate, or any combination thereof.

In some embodiments, the at least one polyphenol may be isolated or purified from, or provided in the form of, a plant extract (e.g., a tea). Examples of plant sources suitable to generate extracts for the nutraceutical compositions described herein include, but are not limited to, green tea, black tea, pomegranate, acai, blackberries, blueberries, raspberries, rosemary, berberine, *Berberis* sp., *Garcinia* spp., Chinese gall nut, *Gallae chinensis*, *Rhus chinensis*, *Rhus semialata* galls, ginger, grape seed, sage, or any combination thereof. Methods for preparing plant extracts are known in the art as described in, e.g., U.S. Pat. No. 6,746,695 (incorporated by reference for this disclosure), In some embodiments, an extract is prepared by simple brewing in which plant material (e.g., green tea) is dissolved in boiling water for at least five minutes to extract one or more polyphenols.

In some embodiments the effective amount of the at least one polyphenol is from about 0.001% to about 20% (w/v) or (w/w) with respect to the total composition, or other ranges as previously described herein. In one embodiment, the at least one polyphenol is provided as green tea (*Camelia sinensis*). In some cases, the green tea is provided as a green tea solution.

In some embodiments, the reactive oxygen species in the above-mentioned nutraceutical composition is hydrogen peroxide, nitric oxide, peroxyl radical, or peroxynitrite anion, singlet oxygen, hydroxyl radical, or any combination thereof. Alternatively, the reactive oxygen species may be selected from oxidants, oxidizing agents, decoloring and bleaching agents used in foods or animal feeds. Alternatively, the reactive oxygen species may be a percarbonate, a perborate, sodium peroxide, calcium peroxide, a peroxymonosulfate, or a urea-peroxide complex. Alternatively, the reactive oxygen species may be hypochlorite, bromate, or iodate supplied as any of their respective sodium, potassium, or calcium salts. Alternatively, the reactive oxygen species may be a concentrated aqueous solution of hydrogen peroxide containing >10 weight percent of hydrogen peroxide. Alternatively, the reactive oxygen species may be ozone, oxone, or a dioxirane. Alternatively, the reactive oxygen species may be benzoyl peroxide, peroxy acetic acid, nitrogen dioxide, chlorine, chlorine dioxide or azodicarbonamide. Alternatively, the reactive oxygen species may be any combination of the forgoing. The reactivity or activity of any of the forgoing may be modulated by pH adjustment or exposure to light. In some embodiments, the reactive oxygen species in the nutraceutical composition ranges from about 0.0001% to about 10% (w/v) or (v/v) or (w/w) with respect to the total composition, or other ranges as previously described herein. In one embodiment, the reactive oxygen species to be combined with the at least one polyphenol is hydrogen peroxide at a final concentration in the composition of about 0.01% to about 0.08% (v/v) or (w/v), e.g. about 0.01%, 0.02%, 0.03%, 0.04%, 0.05%, 0.06%, 0.07%, 0.08%, or another percentage (v/v) or (w/v) of hydrogen peroxide as described herein.

As used herein, the amount of the reactive oxygen species includes both "free" reactive oxygen species and reactive oxygen species that might be bound to, reacted with, or otherwise made unavailable by other components of the composition. The amount of free and bound reactive oxygen species is calculated with respect to the amount of reactive oxygen species added during the course of making the composition. The amount of free reactive oxygen species, including hydrogen peroxide, in a composition can be measured in several routine ways. For example, these include commercially available electronic meters, test strips, and various titration protocols. In one embodiment, a prerequisite of being able to measure the hydrogen peroxide content is that it is available in solution to undergo the test chemistry. Specifically, any hydrogen peroxide that is bound to, reacted with, or otherwise made unavailable by another component of the mixture would not be detected. In the polyphenol compositions of the invention that are made with hydrogen peroxide, free hydrogen peroxide is readily detected in the final product. Thus, in certain embodiments, the invention provides polyphenol compositions comprising a free reactive oxygen species present in the composition in a proportion relative to the total amount of the reactive oxygen species added to the composition, wherein the proportion of free reactive oxygen species to the total amount of free and bound reactive oxygen species (i.e., total amount of the reactive oxygen species added to the composition) is about 25% to about 100%, about 50% to about 100%, about 75% to about 99%, about 95% to about 98%, about 96% or about 97. Implicit in this determination is that in some embodiments the ROS detected may be in a different chemical form than what was originally added, e.g. the acid-base and disassociation reactions of various peroxide salts listed supra.

In other embodiments, the nutraceutical composition is based on specific concentrations of at least one polyphenol and of at least one reactive oxygen species, or additionally the specific concentrations and relative proportions of the at least polyphenol and the at least one reactive oxygen species to each other. Certain specific concentrations and/or proportions have been found to provide superior effects in human subjects as compared to nutraceutical compositions that lack either or both the at least one polyphenol, and at least one reactive oxygen species, or have different amounts and/or proportions of these active ingredients. (For example, see Example 1.) The specific concentrations of the at least one polyphenol and the at least one reactive oxygen species in the nutraceutical composition that can provide superior results can be, for example, from about 0.001% to about 0.009%, from about 0.002% to about 0.008%, from about 0.003% to about 0.007%, from about 0.004% to about 0.006%, from about 0.003% to about 0.005%, or about 0.003%, 0.004%, or 0.005% of at least one polyphenol, and from about 0.01% to less than 1%, from about 0.01% to about 0.5%, from about 0.01 to about 0.09%, from about 0.02% to about 0.08%, from about 0.03% to about 0.08%, from about 0.03% to about 0.07%, from about 0.04% to about 0.06%, or about 0.05%, 0.06%, or 0.07% of at least one reactive oxygen species. The superior results of such compositions can be determined by assessing the rapidity of resolution of unformed stools in a human subject suffering from diarrhea. For example, after oral administration of the nutraceutical composition to a human subject suffering from diarrhea, superior or unexpected results are manifested when a subject does not have an unformed stool (i.e., time to last unformed stool after ingestion) as soon as about 5 minutes, 15 minutes, 30 minutes, 45 minutes, 1 hour, 2 hours, 3 hours, 4 hours, 5 hours, 6 hours, to about 6.5 hours after ingestion of the nutraceutical composition. Alternatively, after oral administration to a human subject suffering from diarrhea, superior or unexpected results are manifested when a subject suffering from diarrhea is prevented from having an unformed stool at least 2-fold, 3-fold, 4-fold, 5-fold, 6-fold, 7-fold, 8-fold, 9-fold, or 10-fold or more faster as compared to a subject suffering from diarrhea who ingests a nutraceutical composition that does not comprise a reactive oxygen species and/or does not comprise at least one polyphenol or has concentrations and/or relative proportions of the at least one polyphenol and the at least one reactive oxygen species that differ from the concentrations as described above in this paragraph. In certain of these embodiments, the at least one reactive oxygen species that provides a superior, unexpected, or synergistic effect is hydrogen peroxide.

In one embodiment, the nutraceutical composition that provides superior, unexpected, or synergistic results with respect to the rapidity of unformed stool resolution in a human or other animal suffering from diarrhea comprises water, at least one polyphenol at a final concentration of about 0.003-0.005%, and hydrogen peroxide at a final concentration of about 0.04-0.07% or from about 0.03-0.08%. This composition can further comprise potassium sorbate at a concentration of about 0.01 to about 0.02%, sodium dihydrogenphosphate at a concentration of about 0.1-0.2%, and a pH at 4.5-5.0. This composition can further comprise additional ingredients such as flavorings, caffeine, vitamins. minerals, and other non-active ingredients. In one embodiment, the one or more polyphenols are polyphenols from a green tea extract and a pomegranate peel extract.

In some embodiments, the invention provides a liquid nutraceutical composition comprising or consisting essentially of at least one polyphenol present at a concentration of from about 0.003% to about 0.005% and at least one reactive oxygen species present at a concentration from about 0.05% to about 0.06%, wherein when orally administered to a subject suffering from acute gastroenteritis the subject does not have an unformed stool as soon as about 1.5 hours. In one embodiment, the polyphenols are from refined extracts derived from crude green tea and pomegranate rind extracts. In one embodiment, the at least one reactive oxygen species is hydrogen peroxide.

In some embodiments, the invention provides a liquid nutraceutical composition comprising or consisting essentially of at least one polyphenol present at a concentration of about 0.003% to about 0.005% and at least one reactive oxygen species present at a concentration of about 0.01 to about 0.02%, wherein when orally administered to a subject suffering from acute gastroenteritis the subject does not have an unformed stool as soon as about 6.5 hours. In one embodiment, the polyphenols are from refined extracts derived from crude green tea and pomegranate rind extracts. In one embodiment, the at least one reactive oxygen species is hydrogen peroxide.

In some embodiments, the nutraceutical composition is a clear, homogeneous solution comprising: (a) one or more plant extracts each comprising one or more polyphenols, or one or more isolated or purified polyphenols (b) one or more reactive oxygen species, and (c) water. In some embodiments, the nutraceutical composition is a product made by a process comprising mixing one or more plant extracts (when the extracts are already in solution form, dry form, or gel form) that comprise one or more polyphenols with one or more reactive oxygen species and water, and treating said mixture. The treating step can comprise one or more steps, including heating the mixture, boiling the mixture, and filtering said mixture to remove any particulates.

In some embodiments, where the nutraceutical composition is to be provided as a solution, the at least one polyphenol and the reactive oxygen species are combined at a first concentration and allowed to react for a period of time ranging from about one minute to about three hours, e.g., about 5 minutes, 10 minutes, 15 minutes, 30 minutes, 45 minutes, one hours, 1.5 hours, 2 hours, 2.3 hours, 2.7 hours, or another reaction period. After the reaction period, the reacted solution is then diluted so as to prevent overreaction between the at least one polyphenol and the reactive oxygen species. Suitable dilutions range from about a 5 fold dilution to about a 1000 fold dilution, e.g., a 20 fold, 25 fold, 30 fold, 50 fold, 75 fold, 80 fold, 200 fold, 300 fold, 400 fold, 500 fold, 700 fold, or another dilution ranging from about 10 fold to about 1000 fold dilution. Suitable nutraceutically acceptable diluents include but are not limited to, purified water, tea, fruit juice, and carbonated beverage. In one embodiment, the diluent is green tea. In some embodiments, the combination of at least one polyphenol and a reactive oxygen species does not include the addition of an active oxidoreductase, catalase, peroxidase, phenoloxidase, tyrosinase, metal catalyst, or any combination thereof.

The bleaching of polyphenol comprising plant extracts, including green tea and pomegranate peel extracts, leads to the partial removal and to oxidative transformations of the main lipophilic extractives families found in unbleached pulps; fatty acids and sterols. In general, some unsaturated compounds are partially degraded while saturated ones were stable. The extracts of the bleaching filtrates are mainly composed of phenolic compounds, whereas undesired lipophilic extractives are reduced. Furthermore, a reduction in astringency, bitterness, and color are observed. These findings relate to other bleaching processes such as in Sylvestre et al., "Effect of Oxygen, Ozone and Hydrogen Peroxide Bleaching Stages on the Contents and Composition of Extractives of *Eucalyptus globulus* Kraft Pulps." *Bioresource Technology*, (2006), 97:402-428; and Ferrer et al., "Modeling of $H_2O_2$ Bleaching", *Bioresources*, 2011, 6(2), 1298.

In some embodiments, the reactive oxygen species also provides the effect of attenuating a disagreeable flavor or fragrance including bitterness and astringency. In some embodiments, the reactive oxygen species also provides the effect of modifying the beverage color or appearance, such as in a bleaching step during production. In some embodiments, the reactive oxygen species has facilitated the removal of other extractives that would otherwise interfere with the biological activity of the nutraceutical composition. In some embodiments, the reactive oxygen species is added to remove fatty acids, aliphatic compounds, alcohols, sterols, and phenolic compounds.

In some embodiments, the nutraceutical composition is made by a process comprising a polyphenol extraction process that includes a filtration or similar separation step after the addition of a reactive oxygen species. In some embodiments, the nutraceutical composition is made by a process comprising a polyphenol extraction process that includes a filtration or similar separation step before the addition of a reactive oxygen species. Polyphenol extraction processes are well known in the art, such as those described in Santos-Buelga, C., et al., "Extraction and isolation of phenolic compounds," *Methods Mol. Biol.,* 2012, 864:247-64, the contents of which are hereby incorporated-by-reference. Standard extraction processes, include but are not limited to methods using water, boiling water, methanol, methanol/formic acid, methanol/water/acetic acid, etc. Liquid liquid extraction and solid phase extraction can be conducted with chromatography. Other techniques include ultrasonic extraction, heat reflux extraction, microwave-assisted extraction, critical carbon dioxide, pressurized liquid extraction, and use of ethanol in an immersion extractor. Concentration can be made by removal of volitiles in vacuo. Further purification can optionally be achieved by preparative chromatography or other absorptive processes.

In some embodiments where the nutraceutical comprises a preservative, the preservative is selected from among the common salts of benzoate, sorbate, propionate, nitrate, hydrogen peroxide, or EDTA (ethylenediaminetetracetic acid). The effects of the preservative can be optimized, for example, when the final pH of the composition is adjusted to be between 3 and 6.

In some embodiments, the pH of the final nutraceutical composition has been adjusted to be between 3 and 6 by the addition of phosphoric, acetic, or citric acids.

In some embodiments, the nutraceutical composition comprises a flavoring, such as an extract of licorice, chamomile, vanilla, quinine, mentha species, caffeine, gotu cola, lemongrass, malt, cardamom, rose hips, berries, and also artificial sweeteners.

In some cases, the nutraceutical composition consists essentially of an effective amount of the at least one polyphenol and the reactive species to treat a subject suffering from diarrhea such that the subject does not have an unformed stool later than about 5 minutes to about 6.5 hours after ingestion of the nutraceutical composition, e.g., about 5, minutes, 15 minutes, 30 minutes, 45 minutes, 1 hour, 2 hours, 2.5 hours, 3 hours, 4 hours, 4.5 hours, 5 hours, 5.5 hours, 6 hours, 6.5 hours, or another period from about 5 minutes to about 6.5 hours following ingestion of the nutraceutical composition.

In another embodiment, the nutraceutical composition is a product made by the process of three sequential main steps (each main step can itself comprise substeps): (1) Dissolution by heating step, (2) Clarification and Refinement steps, and (3) Formulation. In some embodiments, the nutraceutical composition product made by this process, when orally administered to a subject suffering from acute gastroenteritis, is capable of stopping unformed stools from the subject as soon as about 1.5 or about 6.5 hours.

In certain embodiments, in the dissolution by heating step, one or more polyphenol comprising extract(s) are mixed into water and heated, where the weight to volume (w/v) ratio (g/100 mL) of the extract(s) to water can be between about 0.001% to about 20%, about 0.01% to about 10%, about 0.1% to about 5%, about 0.5% to about 2.5%, about 0.5% to about 1.5%, about 1% to about 1.5%, about 0.5%, about 0.6%, about 0.7%, about 0.8%, about 0.9%, about 1.0%, about 1.1%, about 1.2%, about 1.3%, about 1.4%, about 1.5%, about 1.6%, about 1.7%, about 1.8%, about 1.9%/o, about 2.0%, about 2.1%, about 2.2%, about 2.3%, about 2.4%, and about 2.5%. The heating can involve, for example, bringing the extract in water solution to boiling, and continuing the heating for a period of about 1 to 60 minutes, and then mixing while allowing the solution to cool to a temperature of about 35-65° C. In certain embodiments, the continued heating can be conducted for a period of about 1-30, about 1-25, about 1-20, about 1-15, about 1-10, about 1-5, about 10, about 9, about 8, about 7, about 6, about 5, about 4, about 3, about 2, or about 1 minute. In certain embodiments, the mixing after boiling continues until the solution is cooled to a temperature of about 35° C., 40° C., 45° C., 50° C., or 55° C.

In certain embodiments, in the refinement and clarification steps, the solution from the dissolution by heating step is clarified by centrifugation or vacuum filtration. The centrifugation can occur at a speed of at least 1000 rpm, 2000 rpm, 3000 rpm, 4000 rpm, or 5000 rpm or more; for at least about 1 minute, 2 minutes, 3 minutes, 4 minutes, 5 minutes, 6 minutes, 7 minutes, 8 minutes, 9 minutes, 10 minutes or more; at a temperature less than about 45, 40, 35, 30, or 25° C. After centrifugation or vacuum filtration (through an appropriate filter to remove non-dissolved solids), the centrifugate or filtrate solution is recovered and centrifuged or filtered solids are disposed. In certain embodiments, the recovered centrifugate or filtrate solution is refined by adding food grade hydrogen peroxide with stirring for a final concentration of about 2-15%, about 5-10%, about 2%, about 3%, about 4%, about 5%, about 6%, about 7%, about 8%, about 9%, or about 10% of hydrogen peroxide (v/v). In certain embodiments the volatile components are removed by lyophilization, rotory evaporation, spray drying, or a similar process, and the resultant material is reconstituted by addition of DI water. In this reconstitution step the resultant solution has a total polyphenol content of about 0.01-5%, about 0.05-2%, about 0.1-1.5%, or about 0.4-1%. If in certain embodiments a haze or turbidity is observed the extract may be further clarified by vacuum filtration using, for instance, celite or kieselguhr as filtration aids.

In certain embodiments, in the formulation step, the resultant solution from the refinement and clarification steps is formulated for bottling. For example, the resultant solution from the refinement and clarification steps is diluted with deionized (DI) water about 0.5-fold, 1-fold, about 1.5-fold, about 2-fold, about 2.5-fold, about 3-fold, about 3.5-fold, about 4-fold, about 4.5-fold, or about 5-fold. The pH is then adjusted to a range of about 3.0 to about 4.0, where the pH adjustment can be conducted with standard acids, such as $H_3PO_4$. After this first pH adjustment, the solution can be aliquoted for addition with preservatives or flavorings or the like. For example, to an aliquot, potassium sorbate can be added for a final percentage (wt/wt solution) of about 1-3%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%6, or 3% of potassium sorbate. To the aliquot with potassium sorbate, 1M monobasic sodium phosphate solution can be added in a percentage relative to the aliquot volume of about 10-100%, 15%, 20%, 25%, 30%, 31%, 32%, 33%, 40%, 50%, 60%, 75%, 85%, or 100% (v/v). Then, optionally, flavorings may be added. Afterwards, the aliquot with potassium sorbate and sodium phosphate is diluted about 25-40-fold, about 25-fold, about 30-fold, about 33-fold, about 35-fold, about 43-fold, about 44-fold, about 45-fold, about 50-fold, about 55-fold, about 65-fold, or about 75-fold with DI water. Final pH adjustment is then conducted with standard acids, such as phosphoric acid, to give a final pH of about 4.5-5.5, about 4.5, about 4.6, about 4.7, about 4.8, about 4.9, about 5.0, about 5.1, about 5.2, about 5.3, about 5.4, or about 5.5. Lastly, this solution may be bottled as a nutraceutical composition.

Thus, in certain embodiments, a nutraceutical composition is a product made by the process comprising: (1) dissolving one or more polyphenol comprising extract(s) into water by mixing and heating; (2) clarifying or removing non-dissolved solids from the resultant solution of step (1); (3) refining the resultant solution of step (2) by adding a reactive oxygen species such as hydrogen peroxide; and (4) formulating the resultant solution of step (3) by adding a preservative, adding flavoring agents, diluting with water, and adjusting the pH.

In certain embodiments, a nutraceutical composition capable of stopping unformed stools from a subject suffering from acute gastroenteritis as soon as about 1.5 or about 6.5 hours, is a product made by the process comprising: (1) dissolving one or more polyphenol comprising extract(s) into water by mixing and heating, wherein the polyphenol comprising extract(s) is dissolved in water for a final concentration of about 1.0% to about 2.5% (w/v; g/100 mL), wherein the heating comprises boiling for about 5 minutes followed by mixing while cooling the solution to about 50° C.; (2) clarifying or removing non-dissolved solids from the resultant solution of step (1), wherein the temperature of the resultant solution of step (1) is kept below about 40° C.; (3) refining the resultant solution of step (2) by adding hydrogen peroxide at a final concentration of about 7%, and (4) formulating the resultant solution of step (3): (i) adjusting the pH of the diluted solution of step (4)(i) to a pH within about 3.3 to about 4.0; (ii) diluting the resultant solution of step (3) about 120-200-fold with water; (iii) adding potassium sorbate to the pH adjusted solution of step (4)(ii) at a final concentration of about 0.03% to about 0.05% potassium sorbate (v/v); (iv) adding 1M monobasic sodium phosphate to the resultant solution of step (4)(iii) in an amount where the 1M monobasic sodium phosphate constitutes about 1% of the solution (v/v); and (v) adjusting the pH of the resultant solution of step (4)(iv) to a pH of about 5.

Also disclosed herein are kits that kit consists essentially of (i) a first container containing a volume of a first nutraceutically acceptable solution comprising at least one polyphenol; (ii) a second container comprising a volume of a second solution containing a reactive oxygen species; and (iii) instructions to mix the first solution and second solution to obtain a third solution, and to ingest the third solution to thereby treat the gastrointestinal condition, inflammatory condition, or immune condition; wherein the first or second container can accommodate the combined volume of the first solution and the second solution. Optionally, the kits may also include a nutraceutically acceptable diluent as described herein. In some cases, the instructions will include a reaction time during which the at least one polyphenol and the reactive oxygen species are allowed to react prior to dilution or ingestion of the solution as described herein. In some cases, the instructions will also provide instructions to dilute the reacted polyphenol and reactive oxygen species after the foregoing reaction period. Suitable containers for such kits include, for example, bottles, vials, syringes, and test tubes. The containers can be formed from a variety of materials such as glass or plastic. A label may be associated with the kit container. A label can be on a container when letters, numbers or other characters forming the label are attached, molded or etched into the container itself, a label can be associated with a container when it is present within a receptacle or carrier that also holds the container, e.g., as a package insert. A label can be used to indicate that the contents are to be used for a specific therapeutic application. The label can also indicate directions for use of the contents, such as in the methods described herein.

Methods of Treatment

Also described herein are methods for using the nutraceutical compositions described herein to treat a subject or animal suffering from a gastrointestinal condition, an inflammatory condition, or an immune condition, the method comprising providing to the subject (i) a first container containing a volume of a first nutraceutically acceptable solution comprising at least one polyphenol; (ii) a second container comprising a volume of a second solution containing a reactive oxygen species; and (iii) instructions to mix the first solution and second solution to obtain a third solution, and to ingest the third solution to thereby treat the gastrointestinal condition, inflammatory condition, or immune condition, wherein the first or second container can accommodate the combined volume of the first solution and the second solution. In some embodiments, the method comprises providing to the subject a pre-mixed solution comprising the at least one polyphenol and at least one reactive oxygen species.

In one aspect, the invention provides a method for treating a gastrointestinal condition, an inflammatory condition, or an immune condition, the method comprising orally administering to a subject or animal in need a nutraceutical composition as described herein in amount sufficient to treat one or more symptoms of the relevant condition. Where the method is for treating diarrhea or a condition that comprises diarrhea as a symptom, the nutraceutical is orally administered in an amount sufficient to prevent the subject from having an unformed stool in about 5 minutes to about 6.5 hours after ingestion of the nutraceutical composition, e.g., about 5, minutes, 15 minutes, 30 minutes, 45 minutes, 1 hour, 2 hours, 2.5 hours, 3 hours, 4 hours, 4.5 hours, 5 hours, 5.5 hours, 6 hours, 6.5 hours, or another period from about 5 minutes to about 6.5 hours following ingestion of the nutraceutical composition.

In some embodiments the gastrointestinal condition is diarrhea, Crohn's disease, diverticulosis, diverticulitis, *Helicobacter pylori* (stomach infection), lactose intolerance, irritable bowel syndrome (IBS), ulcerative colitis (UC), colon polyps and cancer, and unexplained abdominal pain. In one embodiment, the gastrointestinal condition is acute or chronic diarrhea. In other embodiments, the inflammatory condition is asthma, sinusitis, otitis media, or bacterial conjunctivitis, an autoimmune disease, rheumatoid arthritis, sarcoidosis, celiac disease, vasculitis, or interstitial cystis. In other embodiments, the immune condition is lupus, multiple sclerosis, Type I diabetes, allergies, Graves' Disease, scleroderma, eosinophilic gastroenteritis, Hashimoto's thyroiditis, or inclusion body myositis. In other embodiments, the nutraceutical composition comprises an effective amount of the at least one polyphenol and the reactive species to treat a subject suffering from the effects of chronically elevated systemic levels of serotonin, such as osteoporosis. In other embodiments, the nutraceutical composition comprises an effective amount of at least one polyphenol and the reactive species to treat a subject suffering from the side effects of elevated systemic serotonin levels secondary to various medicines, such as Selective serotonin reuptake inhibitors (SSRIs), which lead to gastrointestinal symptoms such as nausea, vomiting, diarrhea, gas & bloating, GERD, upset stomach, and heartburn. In other embodiments, the nutraceutical composition comprises an effective amount of at least one polyphenol and at least one reactive species to provide inhibition or down regulation of epithelial ion transport across colonic epithelial or other cells to treat a subject suffering from the side effects of intestinal inflammation and intestinal crypt fluid secretion which lead to gastrointestinal symptoms such as nausea, vomiting, diarrhea, gas and bloating, GERD, upset stomach, and heartburn.

In cases of human or animal health where antibiotics are conventionally used the compositions and products of the invention can be substituted for and/or co-administered with antibiotics to achieve a similar or better outcome. This outcome may be a reduction of symptoms or improved health such as measured by weight gain.

Humans and other animals are treated with antibiotics for a multitude of reasons. These antibiotic treatment regimens modulate the human microbiome including not only the prevalence of various bacterial species, but also the coexisting fungi and viruses. Various flavonoids have been demonstrated to have both positive and negative impacts on specific bacterial species as described herein. The clinical data provided herein in Example 1 have unexpectedly demonstrated alleviation of digestive disease symptoms which parallel those often achieved by antibiotic treatment. These data demonstrate that polyphenol compositions may be potential substitutes or supplements for antibiotic treatments. Another application of the compositions and products of the invention is to promote weight gain and reduce disease pressure in animal rearing.

In another embodiment, the invention provides a method for increasing the biological activity of reactive oxygen species, such as peroxides, in vivo by administering one of the polyphenol comprising compositions described herein. For example, polyphenols at various levels of condensation inhibit peroxidase enzymes that would normally decompose available hydrogen peroxide. Similarly the peroxidase activity of metal ions can be inhibited by chelation by the polyphenols. Without being bound by theory, the polyphenols present in the compositions of the invention may also contribute to the ability of hydrogen peroxide or other oxidizing species to persist long enough to reach the sites of action in the GI tract. Thus, in one embodiment, the invention provides a polyphenol comprising composition as described herein that comprises free hydrogen peroxide. "Free" hydrogen peroxide refers to hydrogen peroxide in an unbound state. The hydrogen peroxide content of a solution can be measured in several ways. These include commercially available electronic meters, test strips, and various titration protocols. A prerequisite of being able to measure the hydrogen peroxide content is that it is available in solution to undergo the test chemistry. Specifically, any hydrogen peroxide that is bound to another component of the mixture would not be detected. In the polyphenol compositions of the invention that are made with hydrogen peroxide, free hydrogen peroxide is readily detected in the final product.

In another embodiment, the invention provides methods of inhibiting gastrointestinal motility by administering a polyphenol-comprising composition as described herein. Gastrointestinal motility assays are known in the art, for example, as described in Balemba, O., et al., *Neurogastroenterol Motil.*, 2010, 22(12):1332-1339, and Qnais E., et al., *Pharmaceutical Biology*, 2007, 45(9):715-720, which are hereby incorporated by reference at least for their disclosure on gastrointestinal motility assays. In particular, the polyphenol compositions of the present invention can inhibit gastrointestinal motility at polyphenol concentrations orders of magnitude lower than prior polyphenol extract administrations, such as for example, at least 10-fold less, 20-fold less, 50-fold less, 100-fold less, or 200-fold less of polyphenol for achieving about the same relative inhibition of distance of gastrointestinal motility as measured by standard assays. For example, as described in the cited Qnais et al. reference in this paragraph, a standard gastrointestinal motility assay involves the administration of charcoal food to animals, sacrificing the animals, and examining the small intestine for measurement of the distances traversed by the front of the charcoal food, where the distance is calculated as a percentage of the whole intestine length (from the plylorus to the cecum).

In some cases, the instructions will include a reaction time during which the at least one polyphenol and the reactive oxygen species are allowed to react prior to dilution or ingestion of the solution as described herein. Suitable reaction times prior to treatment of a subject suffering from any of the above-mentioned conditions ranges from at least about one minute to about one hour prior to treatment of the subject. e.g., at least about 2 minutes, 3 minutes, 4 minutes, 5 minutes, 7 minutes, 10 minutes, 15 minutes, 20 minutes, 30 minutes, 35 minutes, 40 minutes, 50 minutes, or a another period from at least about 1 minute to about one hour prior to treatment of the subject in need thereof.

In some cases, methods of treatment include diluting the reacted polyphenol and reactive oxygen species after the foregoing reaction period. Depending on the condition to be treated and its severity, suitable dilutions range from a 1:50 fold to about a 1:1000 fold dilution prior to ingestion by a subject in need of treatment, e.g., about a 1:60, 1:80, 1:100, 1:200, 1:300, 1:350, 1:500, 1:600, 1:700, 1:900, or another fold dilution from about 1:60 to 1:1000 fold prior to treatment.

While not wishing to be bound by theory, it is believed that the nutraceutical compositions and methods described herein may, for at least some conditions, provide their therapeutic effect by acting at one or more points in the pathways described below. Further, in some embodiments of the treatment methods described herein, a subject is treated by co-administering a nutraceutical composition disclosed herein and a pharmaceutical agent that acts in the 5-HT/Serotonin signaling pathway and/or in modulating ion influx/efflux across epithelial cell barriers. In some cases, where such agents are co-administered, a lower dose of the pharmaceutical agent is administered than would be administered to treat the same condition with the pharmaceutical agent alone. Thus, by combining the therapeutic benefits of these different types of compositions, it may be possible to lessen adverse side effects associated with such pharmaceutical agents when given at standard doses.

Serotonin

Serotonin can elicit a number of actions on cells and tissues in the gut, including epithelial secretion, direct smooth muscle activation or relaxation, stimulation of extrinsic and intrinsic sensory neurons, and activation of cholinergic neurons that contract smooth muscle. A number of subtypes of 5-HT receptors, with specific distributions in the intestines, are responsible for the multitude of actions that can be elicited by 5-HT. Serotonin receptors that have been identified to date include 5-HT1A-E, P, 5-HT2A,B,C, 5-HT3, 5-HT4, 5-HT5, 5-HT6, and 5-HT7. The 5-HT3 and 5-HT4 receptors are the most thoroughly understood subtypes with regard to gut function, and at this point they are the primary pharmacotherapeutic targets for the treatment of gastrointestinal (GI) disorders. Several medications that affect these receptors have been approved for the treatment of nausea, vomiting, pain, discomfort, and increased or decreased gastrointestinal motility 5-HT is released when EC cells are activated by stimuli, such as distension or chemical signals; the resultant release of 5-HT increases motility of the gut. Conversely, dysregulation of the GI 5-HT signaling system is involved in the etiology of several conditions such as functional gastrointestinal disorders, chemotherapy induced emesis, and heart valve damage.

After release of 5-HT from EC cells or neurons, it is inactivated by either (1) reuptake into enterocytes, neurons, or platelets through reuptake, which is controlled by a serotonin transporter protein (SERT), which is one of the solute carrier family of proteins (SLC6A4). Following reuptake, 5-HT is metabolized to 5-hydroxyindole acetic acid (5-HIAA), which is excreted in the urine.

5-HT has been implicated in the pathophysiology of GI disorders such as the carcinoid syndrome, a rare disorder, and irritable bowel syndrome (IBS), a most common GI disease. Abnormalities of serotonergic signaling, including altered expression of TpH-1 and 5-HT reuptake transporter, and altered release of 5-HT, have been implicated in IBS pathogenesis.

One of the most consistent findings is an increase in plasma 5-HT in diarrheal diseases such as carcinoid diarrhea and IBS-D, including in children with IBS-D, and reduced levels in IBS-C. In addition, some reports document alterations in tissue levels of 5-HT and of the reuptake protein SERT in IBS. Thus, for example, post-infectious IBS is associated with increased 5-HT content in rectal biopsies; on the other hand, tissue expression of SERT in rectal or colonic biopsies is inconsistent in different reports in the literature. Reduced platelet SERT has been reported with increased plasma 5-HT in IBS-D. and platelet SERT influences the response to the 5-HT3 receptor antagonist, alosetron.

As 5-HT does not freely cross the blood-brain barrier due to its positive charge at physiological pH, centrally and peripherally synthesized 5-HT can function in relative isolation. This has enabled the investigation and therapeutic targeting of the peripheral effects independent of the central effects of 5-HT.

5-HT functions centrally as a neurotransmitter within the peripheral nervous system (CNS). It is synthesized utilizing TPH1 and released by enteroendocrine cells and neurons of the raphe nuclei and has been shown to influence a range of behavioral, physiological and cognitive functions. These effects are mediated by seven families of membrane-bound 5-HT receptors (5-HT1 to 5-HT7) and are tightly regulated by a plasma membrane 5-HT transporter (5-HTT [also known as SERT]). The SERT regulates the duration of 5-HT activity by actively transporting 5-HT using transmembrane ion gradients of $Na^+$, $Cl^-$ and $K^+$, and an internal negative membrane potential.

The most consistent findings are the increase in plasma 5-HT in diarrheal diseases such as carcinoid diarrhea and IBS-D, including in children with IBS-D, and reduced levels in IBS-C. In addition, some reports document alterations in tissue levels of 5-HT and of the reuptake protein SERT in IBS. Thus, for example, post-infectious IBS is associated with increased 5-HT content in rectal biopsies; on the other hand, tissue expression of SERT in rectal or colonic biopsies is inconsistent in different reports in the literature. Reduced platelet SERT has been reported with increased plasma 5-HT in IBS-D, and platelet SERT influences the response to the 5-HT3 receptor antagonist, alosetron.

As 5-HT does not freely cross the blood-brain barrier due to its positive charge at physiological pH, centrally and peripherally synthesized 5-HT can function in relative isolation. This has enabled the investigation and therapeutic targeting of the peripheral effects independent of the central effects of 5-HT.

5-HT functions centrally as a neurotransmitter within the peripheral nervous system (CNS). Pharmaceutical agents that antagonize the 5-HTT, such as selective serotonin reuptake inhibitors (SSRIs), are clinically popular as they potentiate 5-HT activity and have been shown to effectively relieve depressive symptoms, however SSRIs antagonize SERT in the entire body, rather than just in CNS, and many of the most common side effects are due to the antagonism of SERT outside of the CNS.

Serotonin is an important gastrointestinal signaling molecule. It is a paracrine messenger utilized by Enterochromaffin (EC) cells, which function as sensory transducers. Serotonin activates intrinsic and extrinsic primary afferent neurons to, respectively, initiate peristaltic and secretory reflexes and to transmit information to the central nervous system.

5-HT is involved in the control and modulation of multiple physiological and psychological processes. In the central nervous system (CNS), 5-HT regulates mood, appetite, and other behavioral functions. It is estimated that 95% of the 5-HT in the human body is located in the GI tract, with 90% being in enterochromaffin (EC) cells in the epithelial layer and 5% by a subpopulation of enteric neurons intrinsic to the bowel wall.

Animal studies have revealed that 5-HT, released from EC cells and interneurons, is involved in the control of GI secretion, motility, and visceral perception.

Serotonin is also a neurotransmitter utilized by a system of long descending myenteric interneurons. Serotonin is synthesized through the actions of 2 different tryptophan hydroxylases, TpH1 and TpH2, which are found, respectively, in EC cells and neurons. Serotonin is inactivated by the serotonin reuptake transporter (SERT)-mediated uptake into enterocytes or neurons.

The presence of many serotonin receptor subtypes enables selective drugs to be designed to therapeutically modulate gastrointestinal motility, secretion, and sensation.

In the GI system 5-HT plays a prokinetic role in general, and it is an important mediator of sensation (e.g., nausea and satiety) between the GI tract and the brain.

5-HT Receptors

There are seven main classes of 5-HT receptors, with several subclasses that can be differentiated on the basis of their molecular structure, transduction pathways and functions. To date, the serotonergic receptors of greatest relevance in the GI tract are the 5-HT3 receptors which are ion channels, and the 5-HT4 receptors which have 7 transmembrane domains.

5-HT3 Receptors

The 5-HT3 receptor is a ligand-gated ion channel that causes a rapid and transient excitatory response when activated by 5-HT. Like most ligand-gated ion channels, 5-HT3 receptors quickly desensitize with continuous exposure to an agonist. Within the ENS, 5-HT3 receptors are located on the processes of intrinsic and extrinsic sensory neurons and on the cell bodies of most enteric neurons. Thus, 5-HT3 receptor activation of intrinsic afferent fibers can initiate peristalsis, secretion, and vasodilation in the gut, while extrinsic afferent nerve fiber activation can trigger homeostatic, emetic, and nociceptive reflexes. The wide variety of effects that 5-HT3 receptors have explains why so much effort has been expended to develop selective and effective 5-HT3 receptor antagonists for the treatment of nausea and vomiting associated with chemotherapy and the symptoms of irritable bowel syndrome with diarrheal predominance (IBS-D).

In some embodiments, any of the following agents are co-administered with one of the nutraceutical compositions described herein to treat a subject suffering from a condition described herein (e.g., a gastrointestinal condition).

5-HT3 Receptor Agonists

Because of the location of 5-HT3 receptors in the enteric reflex circuitry, it is plausible that 5-HT3 receptor agonists could act as prokinetics. However, to avoid tachyphylaxis as a result of the rapidly desensitizing property of this receptor and the nausea and vomiting that typically occur in response to Vagal afferent stimulation, it is likely that only partial agonists would be effective pharmacotherapeutic agents. The effects of the partial 5-HT3 agonist MKC-733 have been tested in a gastric emptying assay, but data are lacking with regard to colonic function and sensitivity. This medication is not currently FDA approved.

5-HT3 Receptors Antagonists

Chemotherapeutic agents are known to elicit abnormal 5-HT release in the gut, and 5-HT3 antagonists work, in part, by blocking 5-HT3 receptors on intestinal afferent fibers. A number of 5-HT3 antagonists have been approved by the FDA to decrease the sensation of nausea associated with chemotherapy, including ondansetron, granisetron, dolasetron, and ramosetron. These agents also decrease postprandial motility and visceral sensitivity, therefore, 5-HT3 receptor antagonists have been investigated for use in IBS-D.

Alosetron is a 5-HT3 receptor antagonist that is ten times more potent than ondansetron and was developed specifically for IBS-D. This drug prolongs colonic transit but has minimal effect on colonic visceral sensation in healthy volunteers. Four large randomized, double-blind, placebo-controlled trials have demonstrated that alosetron is associated with a significant improvement in stool frequency, consistency, and abdominal discomfort in women with IBSD. The most common side effect of alosetron is constipation, but of greater concern is an increased incidence of ischemic colitis (0.15 percent) compared with placebo (0 percent), leading to temporary withdrawal of the drug in 2000 by GlaxoWellcome. Further investigation demonstrated that the increase in the incidence of ischemic colitis did not correspond with an increase in mortality, and alosetron was reapproved by the FDA on a restricted basis for refractory cases of IBSD in female patients.

5-HT4 Receptors

The 5-HT4 receptor is a guanine nucleotide binding (G) protein-coupled receptor that leads to protein kinase A (PKA) activation resulting in a prolonged excitatory response. The precise distributions of 5-HT4 receptors in the gastrointestinal tract have not been definitively resolved, but they are clearly located on nerve terminals throughout the intrinsic reflex circuitry of the gut and may be located on sensory nerve terminals in the lamina propria. Activation of presynaptic 5-HT4 receptors results in the facilitation of transmitter release and an augmentation of reflex activity. Thus, stimulation does not initiate motor activity but rather enhances motor function in the intestine. If 5-HT4 receptors are located on the processes of sensory neurons in the lamina propria, they would contribute to the initiation of reflex activity in response to 5-HT release from EC cells. Therefore, 5-HT4 receptor agonists are believed to increase gastrointestinal motility in response to intraluminal stimuli, whereas antagonists suppress motor activity.

5-HT4 Agonists

Tegaserod, an aminoguanidine indole, is a selective partial agonist of 5-HT4 receptors that has been developed for disorders of slow transit. It is unlikely that tegaserod produces receptor desensitization with prolonged use because it is a partial agonist and, consistent with this, has demonstrated sustained clinical benefit. In vivo, tegaserod increases the maximum stimulation of peristalsis, to a lesser extent than that seen with 5-HT stimulation, as expected of a partial agonist. Placebo-controlled clinical trials of tegaserod have shown promise, demonstrating an increase in the overall number of bowel movements and a decrease in the numbers of days without bowel movements. This effect reached significance only in females and there was no significant improvement of abdominal pain. There has been no documented increase in ischemic colitis, gallbladder disorders, or cardiac arrhythmias with the use of tegaserod. Tegaserod is currently FDA-approved for treatment of IBS with constipation predominance (IBS-C) in females and has a Grade A recommendation by the American College of Gastroenterology for chronic constipation in patients under the age of 65. There has been some indication that tegaserod may be useful in chronic colonic pseudoobstruction; however, data remain insufficient to support this use.

Prucalopride is a benzofuran-derived 5-HT4 receptor agonist that stimulates stomach and ascending colonic emptying in healthy volunteers. Randomized, double-blind, placebo-controlled studies have demonstrated an increase in the number of spontaneous bowel movements in response to prucalopride.

5-HT4 Receptor Antagonists

The 5-HT4 receptor antagonist piboserod decreased motility in patients with IBS-D in a small randomized, double-blind, placebo-controlled trial. Overall, animal and human studies have shown that 5-HT4 receptor antagonists have a minimal effect on normal healthy volunteers, but do ameliorate the effects of administered 5-HT or 5-HT4 receptor agonists. These data suggest that piboserod works in disorders of excess 5-HT but not in the healthy population. There is concern that piboserod may cause atrial fibrillation because of its effects on atrial 5-HT4 receptors. As the understanding of gastrointestinal motility disorders expands, there will likely be further development of this class of antagonists because they counteract only the effect of increased serotonin and do not appear to cause secondary gastrointestinal side effects of their own accord.

Tryptophan Hydroxylase Inhibitors

5-HT is synthesized through the actions of the rate-limiting enzyme tryptophan hydroxylase (TpH), of which 2 different types. TpH1 and TpH2, are expressed by EC cells and neurons (in the enteric and central nervous system), respectively. These share ~70% identity and they are ~50% identical to phenylalanine and tyrosine hydroxylases. In enterochromaffin (EC) cells of the gut, TPH1 is primarily expressed; in contrast, TPH2 is expressed exclusively in neuronal cells, including the myenteric plexus.

Serotonergic agents are used in therapy of lower functional gastrointestinal disorders. In IBS-D, alosetron (which blocked the effects at 5-HT3 receptors that are relevant to stimulation of motility and secretion and transmission of pain in the gut) shows considerable efficacy in the relief of urgency, diarrhea and abdominal pain. These agents did not reduce the 5-HT content, production or release from the gut. The early generation 5-HT4 receptor agonists, such as cisapride and tegaserod, reversed slow motility and relieved constipation, but they have been withdrawn because of cardiac or vascular adverse effects. These agents activate receptors on intrinsic cholinergic neurons to stimulate motility without increasing the levels of 5-HT which appears to be deficient in patients with IBS-C or diseases associated with constipation. Newer 5-HT3 receptor antagonists and 5-HT4 receptor agonists are efficacious, appear to be safer than earlier generation agents in these classes, and promise to provide relief for IBS symptoms in patients.

Direct blockade of 5-HT synthesis through inhibition of TPH was also evaluated with a compound called parachlorophenylalanine (pCPA) in humans. The compound proved effective in treating diarrhea in patients with carcinoid syndrome and emesis induced by chemotherapy. However, pCPA treatments have also been linked to depression and other alterations in CNS function, precluding the development of this agent for therapeutic use.

The use of a peripherally acting inhibitor of 5-HT synthesis and/or secretion has great potential for elucidating the role of 5-HT in the control of GI functions in humans.

A novel class of compounds (of which the prototype is LX-1031) is being developed that directly inhibits 5-HT synthesis in enterochromaffin cells, potentially reversing the underlying pathogenetic factor in conditions like IBS-D. This could be an alternative to the application of 5-HT3 receptor antagonists in IBS-D.

The use of compounds that inhibit Serotonin synthesis and/or secretion, in combination with measurements of GI sensorimotor function may permit the evaluation of the role of 5-HT in the control of other GI functions where animal studies showed a role for 5-HT, such as upper GI fasting and postprandial motility, and the control of mechanosensitivity and chemosensitivity of the GI tract in man.

Inhibition of GI 5-HT synthesis could provide therapeutic benefit in patients with carcinoid syndrome, and potentially also in the treatment of chemotherapy-induced nausea and vomiting, 2 conditions in which 5-HT from the GI tract plays a pivotal pathophysiologic role.

Previous studies that measured plasma 5-HT levels after a meal challenge have revealed that exaggerated 5-HT release from the GI tract is present in a subset of IBS patients with diarrhea. This group of patients is more likely to respond to inhibition of 5-HT release or function. The current data in this study suggest that the magnitude of inhibition of 5-HT synthesis determines symptomatic outcome, as revealed by the superior response rates in the group that achieved a 15% decrease in 5-OHIAA excretion during treatment.

The goal of blocking the effects of excessive 5-HT is certainly not new (1). However, prior approaches aimed at the inhibition of the synthesis of 5-HT have been impeded by the central adverse effects of inhibition of brain 5-HT synthesis with consequent affective disorders.

Based on previous studies with 5-HT3 and 5-HT4 receptor antagonists, 5-HT3 receptors are the most likely target for 5-HT in the control of intestinal peristalsis.

The predominant mechanism targeted for IBS-D is the 5-HT3 receptor with antagonists like ramosetron. This class of drugs is associated with ischemic colitis and complications of constipation, and, over a 6.5 year period, only ~28,000 patients received the approved drug, alosetron, in the United States after the implementation of a risk management plan.

LX-1031 is a member of a novel class of orally administrable, small molecule TPH inhibitors, with poor systemic absorption and low penetration through the blood—brain barrier.

Chloride Ion Channels

While the publications described below relate to the study of tannins or hydrogen peroxide in their effect on chloride ion channels, none of the publications provide evidence, for example, of the present invention's findings that certain compositions as described above having specific concentrations and/or relative proportions of both polyphenols and hydrogen peroxide provide synergistic and superior effects for diarrhea resolution in human or animal subjects.

Intestinal Fluid Secretion

Intestinal fluid secretion involves Chloride influx into enterocytes through a $Na^+/K^+/2Chloride$ symporter and $Chloride/HCO_3$-exchanger on the basolateral membrane, and Chloride efflux through apical (lumen-facing) $Ca^{2+}$-dependent, and cAMP-dependent Chloride channels, among which is cystic fibrosis transmembrane conductance regulator protein (CFTR). Basal membrane located $K^+$ channels and a $3Na^+/2K^+$-ATPase pump establish the electrochemical driving force for Chloride secretion. $Na^+$ and water secretion follow passively paracellularly in response to active Chloride secretion. The rate of net intestinal fluid secretion, and hence the severity of secretory diarrhea, is expected to be sensitive to modulators of these transporting systems and to upstream cyclic nucleotide or calcium signaling pathways Bacterial enterotoxins produced by pathogens such as *Vibrio cholerae* and *Escherichia coli* elevate cyclic nucleotide concentrations in enterocytes, resulting in Chloride channel activation and fluid secretion. Among these transport proteins, CFTR has been recognized as one of the most attractive target protein, whose inhibitors are expected to possess therapeutic values in the treatment of cholera.

Apical Membrane Ion Channels

Tradtrantip et al., (2010) (Lukmanee Tradtrantip, Wan Namkung. and A. S. Verkman, "Crofelemer, an Antisecretory Antidiarrheal Proanthocyanidin Oligomer Extracted from Croton lechleri, Targets Two Distinct Intestinal Chloride Channels," *Mol. Pharmacol.* 77:69-78, 2010) focused on targeted inhibitors of the two principal apical membrane Chloride channels in enterocytes: the cystic fibrosis transmembrane regulator conductance (CFTR), a cAMP-stimulated Chloride channel; and calcium-activated chloride channels (CaCCs). Although crofelemer did not affect the initial currents induced by the CFTR and CaCC agonists, increasing concentrations of crofelemer appeared to produce more rapid, although partial, inhibition of CFTR Chloride current. Crofelemer acted as a partial antagonist of CFTR Chloride conductance, with a concentration-dependent rate of inhibition over several minutes. It is unknown why crofelemer inhibition of CFTR Chloride conductance is partial even at very high concentrations. Some possibilities for such partial inhibition include partial external CFTR pore blockade by the large crofelemer molecule and an intrinsically inefficient allosteric inhibition mechanism In addition, crofelemer inhibited chloride secretion in T84 cells in a concentration-dependent manner, which implicated the CaCC protein TMEM16A, which is found in multiple epithelial cells, including intestinal epithelia. This inhibition was nearly complete at high concentrations of crofelemer. These results define a second, distinct luminal membrane Chloride channel target of crofelemer.

Hydrolysable Tannins

Hydrolysable tannins are plant polyphenols commonly found in a variety of plants. They are composed of a central carbohydrate (usually glucoses) esterified with phenolic groups, such as gallic acid (gallotannin) and ellagic acid (ellagitannin). Wongsamitkul, et al., (2010) (Nisa Wongsamitkul. Lalida Sirianant, Chatchai Muanprasat, and Varanuj Chatsudthipong, "A Plant-Derived Hydrolysable Tannin Inhibits CFTR Chloride Channel: A Potential Treatment of Diarrhea," *Pharmaceutical Research*, Vol. 27, No. 3, March 2010) hypothesized that hydrolysable tannins also are inhibitory against CFTR chloride channels in vitro. They demonstrated that a hydrolysable tannin isolated from Chinese gallnuts, penta-m-digalloyl-glucose (PDG) inhibited CFTR function. It was shown that PDG reversibly inhibited CFTR chloride transport activity without altering intracellular cAMP level. An in vivo mouse model of cholera revealed that PDG was effective in inhibiting chloride secretion induced by cAMP and cholera toxin, without effecting intestinal fluid absorption or calcium-activated chloride secretion. PDG was able to inhibit transepithelial active chloride secretion induced by cAMP, while it had no effect on that induced by elevation of intracellular calcium.

$H_2O_2$ Appears to Reduce Chloride Ion Secretion Through an Inhibitory Effect on Basal Membrane $Na^+$-$K^+$-ATPase Chloride ion secretion across the intestinal epithelium requires the coordinated action of several transporters. First, the $Na^+$-$K^+$-ATPase localized to the basolateral membrane is responsible for establishing and maintaining $Na^+$ and $K^+$ gradients across the cell membrane. Second, basolateral K+ channels act to recycle $K^+$, brought into the cell through the activity of the $Na^+$-$K^+$-ATPase, back into the serosal space. Moreover, these channels are important in providing a sustained electrical driving force necessary to maintain chloride secretion. Third, the $Na^+$-$K^+$-2chloride ion cotransporter loads chloride ions into the cells above its electrochemical equilibrium by coupling chloride ion transport to $Na^+$. Last, the apical membrane chloride ion channel(s) conduct chloride ions out of the cell down its electrochemical gradient.

The two key events involved in the chloride ion secretory response are the efflux of $K^+$ ions through basolateral $K^+$ channels and the NKCC1-mediated basolateral uptake of chloride ions (in conjunction with $Na^+$ and $K^+$) that replenishes intracellular chloride ion lost through apical chloride ion channels. The coordinated activation of both of these transporters is required to create the concentration gradient necessary for electrogenic chloride ion secretion to occur.

Chappell et al (2008) (Chappell, A. E., Bunz, M., Smoll, E., Dong, H., Lytle, C., Barrett, K. E., & McCole, D. F., "Hydrogen peroxide inhibits Ca2+-dependent chloride secretion across colonic epithelial cells via distinct kinase signaling pathways and ion transport proteins," *The FASEB Journal.* 2008, 22(6), 2023-2036) investigated the effects of ROS, specifically $H_2O_2$, on $Ca^{2+}$-dependent basal membrane chloride ion secretion across colonic epithelial cells and the signaling pathways activated by $H_2O_2$ that modify epithelial ion transport responses. The data from their study appeared to indicate that $H_2O_2$ inhibits both of these processes. $H_2O_2$ inhibited NKCC1 activity independently of possible effects on apical Chloride channels. The inhibition of $K^+$ efflux and NKCC1 activity likely contributed to the overall inhibitory effect of $H_2O_2$ on $Ca^{2+}$-dependent ion transport in colonic epithelial cells.

Reactive species such as $H_2O_2$ have been previously shown to adversely affect ion channel function, possibly through the oxidation of key sulfhydryls and/or amino acid residues on the channel protein. Alternatively, the $H_2O_2$-induced decrease in chloride conductance may be due to an inhibition of intracellular ATP levels. Chappell (2008) found that $H_2O_2$ acutely activates a basolateral $K^+$ conductance that may account for the observed transient increase in chloride secretion observed immediately following $H_2O_2$ treatment. The authors also concluded that $H_2O_2$ directly inhibited the basolaterally located $Na^+$-$K^+$-ATPase by decreasing intracellular ATP levels. Inhibition of the ion transport processes appears to be dependent on intracellular $Ca^{2+}$ and linked to decreased intracellular ATP levels, which may explain the relatively long onset of the inhibitory effect. In conclusion, the authors stated that the results suggested that the principal effect of $H_2O_2$ on colonic chloride secretion is that of inhibition.

EXAMPLES OF THE INVENTION

Example 1: Human Study Comparing the Time to Last Unformed Stool (TTLUS) in Children and Adults Diagnosed with Acute Gastroenteritis A single dose, double-blind, placebo-controlled, 3-arm study was conducted comparing the Time to Last Unformed Stool (TTLUS) in children and adults diagnosed with acute gastroenteritis.

The Test Material administered in Treatment Arm 1 (n=83) and Treatment Arm 2 (n=37) was an aqueous suspension made from a Refined Extract Blend derived from Crude Green Tea and Pomegranate extracts and hydrogen peroxide. The ratio and total amount of Pomegranate and Green Tea Extracts (2.4 mg/60 mL dose, wherein the total amount of polyphenols in each dose was about 0.004% or about 40 ppm) was held constant in the Arm 1 Test Material and Arm 2 Test Material. The hydrogen peroxide concentration in Arm 1 Test Material was 600 ppm in Arm 1 Test Material (600 ppm is about 36 mg/60 mL dose, or about 0.06% of the dose). The hydrogen peroxide concentration in Arm 2 Test Material was 120 ppm (120 ppm is about 7.2 mg/60 mL dose, or about 0.012% of the dose). The third Arm was the Placebo Arm (n=46) Test Material, which did not contain any polyphenols or hydrogen peroxide, but had a taste and color matched to that of the other treatment arms.

The Median TTLUS for the subjects in Treatment Arm 1, Treatment Arm 2, and the Placebo Treatment Arm were 90 minutes, 6 hours 30 minutes, and 77 hours, respectively. See FIG. 1, where: Treatment Arm 1 results are shown in the top line of the graph ("Refined Extract+hi concentration [ROS] n=83"); Treatment Arm 2 results are shown in the middle line of the graph ("Refined Extract+low concentration [ROS] n=37"); and Treatment Arm 3 results is shown in the bottom line of the graph ("Placebo n=46").

This data shows that subjects diagnosed with acute gastroenteritis who were treated with a Refined Extract Blend derived from a Crude Pomegranate Peel Extract+Crude Green Tea Extract in combination with hydrogen peroxide experienced a clinically significant reduction in Time to Last Unformed Stool vs. Placebo. In addition, the superior results in TTLUS with Arm 1 Test Material vs. Arm 2 Test Material indicates that the higher concentration of hydrogen peroxide in Arm 1 Test Material relative to the amount of polyphenols was important in the overall time to resolution.

We claim:

1. A nutraceutical composition for the treatment of a gastrointestinal condition consisting of a combination of polyphenols extracted from green tea and pomegranate rind and at least one reactive oxygen species, wherein the polyphenol extracts are present at a final concentration from about 0.001% to about 0.009%, wherein the at least one reactive oxygen species is hydrogen peroxide and is present at a final concentration from about 0.01%, to about 0.09%, wherein the gastrointestinal condition is diarrhea and wherein each extract comprises more than 50% polyphenols.

2. The composition of claim 1, wherein after administration, the composition prevents the subject from having an unformed stool as soon as about 5 minutes to about 6.5 hours after ingestion.

3. The composition of claim 2, wherein the composition prevents the subject from having an unformed stool as soon as about 5 minutes, 15 minutes, 30 minutes, 45 minutes, 1 hour, 2 hours, 3 hours, 4 hours, 6 hours, or 6.5 hours after ingestion of the composition.

4. The composition of claim 1, wherein when orally administered to a human subject, the composition prevents the subject from having an unformed stool at least 2-fold faster as compared to a subject suffering from diarrhea who ingests a composition that does not comprise a reactive oxygen species and/or at least one polyphenol, or as compared to a subject suffering from diarrhea who ingests a composition that comprises at least one polyphenol at a final concentration greater than 0.01% and a reactive oxygen species at a final concentration greater than 0.1%.

5. The composition of claim 4, wherein the composition prevents the subject from having an unformed stool at least 3-fold, 4-fold, 5-fold, 6-fold, 7-fold, 8-fold, 9-fold, or 10-fold faster as compared to a subject suffering from diarrhea who ingests a composition that does not comprise hydrogen peroxide and/or a combination of polyphenols extracted from screen tea and pomegranate rind, or as compared to a subject suffering from diarrhea who ingests a composition that comprises at least one polyphenol extracted from green tea and pomegranate rind at a final concentration greater than 0.01% and hydrogen peroxide at a final concentration greater than 0.1%.

6. The composition of claim 1, wherein the combination of polyphenols is present at a final concentration from about 0.002% to about 0.008%, from about 0.003% to about 0.007%, from about 0.004% to about 0.006%, from about 0.003% to about 0.005%, or about 0.004%.

7. The composition of claim 1, wherein the hydrogen peroxide is present at a final concentration from about 0.02% to about 0.08%, from about 0.03% to about 0.08%, from about 0.04% to about 0.07%, about 0.05%, about 0.06%, or about 0.07%.

8. The nutraceutical composition of claim 1, wherein the nutraceutical composition is a powder.

9. The nutraceutical composition of claim 1, wherein the gastrointestinal condition is acute or chronic diarrhea.

10. The nutraceutical composition of claim 9, wherein the composition consists of an effective amount of the combination of polyphenols and the at least one reactive oxygen species such that a subject suffering from the diarrhea does not have an unformed stool later than two hours after ingestion of the nutraceutical composition.

11. The nutraceutical composition of claim 1, wherein the green tea polyphenol is epicatechin, epicatechin gallate, epigaliocatechin, or epigallocatechin gallate, or any combination thereof.

12. The nutraceutical composition of claim 1, further consisting of at least one polyphenol found in black tea, acai, blackberries, blueberries, raspberries, rosemary, berberine, *Berberis* sp., *Garcinia* spp., Chinese gall nut, *Gallae chinensis, Rhus chinensis, Rhus semialata* galls, ginger, grape seed, sage, or any combination thereof.

13. The nutraceutical composition of claim 1, wherein in the combination of polyphenols is a polyphenol of at least one of a punicalagin and/or ellagic acid.

14. The nutraceutical composition of claim 1, wherein the at least one polyphenol is a benzoquinone, a phenolic acid, an acetophenone, a phenylacetic acid, a hydroxycinnamic acid, a coumarin, a phenylpropane, a chromone, a naphthoquinone, a xanthone, a stilbene, an anthraquinone, a flavonoid, an isoflavonoid, a lignan, a neolignan, a bioflavonoid, a catechol melanin, a condensed tannin, or any combination thereof.

15. The nutraceutical composition of claim 1, wherein the nutraceutical composition is selected from the group consisting of a solution, gel, powder, aerosol, or suppository.

* * * * *